United States Patent [19]

Richter et al.

[11] 4,293,707

[45] Oct. 6, 1981

[54] PROCESS FOR PREPARING TRICHLOROPHENOXY ALKANOIC ACID AND HYDROLYZABLE DERIVATIVES THEREOF FREE OF CHLORINATED DIBENZO-P-DIOXINS

[75] Inventors: Sidney B. Richter, Akron; William S. Grove, Doylestown, both of Ohio

[73] Assignee: PPG Industries, Inc., Pittsburgh, Pa.

[21] Appl. No.: 45,549

[22] Filed: Jun. 4, 1979

[51] Int. Cl.$^3$ .............................................. C07C 59/56
[52] U.S. Cl. ..................................... 562/472; 560/62; 564/175
[58] Field of Search .................... 562/472; 260/559 B; 560/62; 531/170

[56] References Cited

FOREIGN PATENT DOCUMENTS 250154   1/1970   U.S.S.R. .............................. 562/427

*Primary Examiner*—Paul J. Killos
*Attorney, Agent, or Firm*—Edward J. Whitfield

[57] ABSTRACT

Trichlorophenoxy alkanoic acid including hydrolyzable salts, aliphatic esters and amides thereof said compounds being free of chlorinated dibenzo-p-dioxins are prepared by liquid phase alkaline condensation of 3-chlorophenol or 3,4-dichlorophenol with an alpha halo alkanoic acid, ester or amide followed by liquid phase chlorination of the condensation product.

5 Claims, No Drawings

PROCESS FOR PREPARING TRICHLOROPHENOXY ALKANOIC ACID AND HYDROLYZABLE DERIVATIVES THEREOF FREE OF CHLORINATED DIBENZO-P-DIOXINS

BACKGROUND OF THE INVENTION 2,4,5-trichlorophenoxy alkanoic acids, especially, 2,4,5-trichlorophenoxy acetic acid (2,4,5-T) and 2-(2,4,5-trichlorophenoxy) propionic acid (Silvex) and the hydrolyzable salts, aliphatic esters and amides thereof are known to be particularly effective herbicides.

2,4,5-trichlorophenoxy alkanoic acid, e.g., 2,4,5-T is typically prepared by condensing 2,4,5-trichlorophenol with haloalkanoic acid e.g., monochloroacetic acid in aqueous alkali metal hydroxide solution as described for example in U.S. Pat. No. 2,598,692. It is also known to prepare 2,4,5-trichlorophenoxy alkanoic acid, e.g., 2,4,5-T, by chlorination of the sodium salt of 2,5-dichlorophenoxy acetic acid as described, for example in U.S. Pat. No. 2,717,907.

The use of both 2,4,5-T and Silvex has been severely curtailed by a recent order of the Environmental Protection Agency since each of these materials contain trace amounts of chlorinated dibenzo-p-dioxins, particularly 2,3,7,8-tetrachloradibenzo-p-dioxin (2,3,7,8-TCDD) which is produced as a by-product in the production of 2,4,5-T and Silvex.

2,3,7,8-TCDD is extremely toxic and there is evidence that it can be fatal to certain species of laboratory animals at levels as low as 0.6 microgram per kilogram of body weight.

Methods have been devised for treating 2,4,5-T or Silvex to reduce their 2,3,7,8-TCDD content which methods are described, for example, in U.S. Pat. Nos. 4,026,917 and 3,840,593. In U.S. Pat. No. 4,026,917 dioxin is removed from 2,4,5-T by adsorption of the dioxin with coconut charcoal. This method is reported to reduce dioxin content of 2,4,5-T to less than 1 part per million. In U.S. Pat. No. 3,840,593 Silvex is subjected to fractional liquid-liquid extraction with a polar liquid solvent which reportedly reduces the dioxin content of the Silvex to typically less than 0.1 part per million. However, such treatment methods though removing a portion of the dioxin from 2,4,5-T or Silvex pose the problem of disposing of the dioxin-contaminated treating material, i.e. the charcoal in the case of U.S. Pat. No. 4,026,917 and the solvent in the case of U.S. Pat. No. 3,840,593. In other words such methods address only the symptoms rather than the cause. Moreover detectable amounts of dioxin remain in the treated 2,4,5-T and Silvex.

With the exception of the process described in copending, commonly assigned U.S. Application Ser. No. 33,349, filed Apr. 26, 1979, means for preparing trichlorophenoxy alkanoic acids, i.e., 2,4,5-T and Silvex including hydrolyzable derivates thereof free of detectable amounts of chlorinated dibenzo-p-dioxins, particularly 2,3,7,8-TCDD, has been unknown to the art, since previous processes have reputedly produced product containing varying quantities, albeit in some cases small quantities, of chlorinated dibenzo-p-dioxins.

For example, current manufacturing processes are believed capable of producing 2,4,5-T containing about 0.01 parts by weight 2,3,7,8-TCDD per million parts by weight, 2,4,5-T. Although 10 parts per billion 2,3,7,8-TCDD in 2,4,5-T might ostensibly appear, for all practical purposes, negligible, due to the extreme toxic nature of 2,3,7,8-TCDD, material containing even such low levels is considered potentially hazardous.

SUMMARY OF THE INVENTION

This invention provides a process for the preparation 2,4,5-trichlorophenoxy acetic acid (2,4,5-T) and 2-(2,4,5-trichlorophenoxy) propionic acid (Silvex) including the hydrolyzable salts, aliphatic esters and amides of these acids, which process avoids the formation of chlorinated dibenzo-p-dioxins as a by-product, by chlorinating the reaction product of 3-chlorophenol or 3,4-dichlorophenol and an alpha haloalkanoic acid, aliphatic ester or amide.

DESCRIPTION OF THE INVENTION

In accordance with this invention 2,4,5-trichlorophenoxy acetic acid (2,4,5-T) including hydrolyzable salts, aliphatic esters and amides thereof and 2-(2,4,5-trichlorophenoxy) propionic acid (Silvex) including hydrolyzable salts, aliphatic esters and amides thereof are prepared by a process comprising:

(a) reacting a chlorinated phenol selected from 3-chlorophenol or 3,4-dichlorophenol with an alpha halo compound represented by the formula

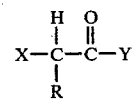

and (b) chlorinating the reaction product of step (a) in the liquid phase to produce the 2,4,5-trichlorinated derivative.

In the above formula, X represents halogen, e.g. chlorine, bromine or iodine; R represents hydrogen or methyl; and Y represents hydroxy, or a hydrolyzable substituent selected from an aliphatic radical containing up to 20 carbon atoms, amide or mono- or di-substituted amide, the substituent of which contains up to 20 carbon atoms. When Y represents an aliphatic radical, the same is preferably an alkoxy or alkoxy-alkoxy group containing up to about 8 carbon atoms, some examples of which are, ethoxy, butoxy, butoxy-ethoxy, iso-octoxy and the like. When Y represents a mono- or di-substituted amide, the substituent is preferably alkyl or alkoxy of up to about 8 carbon atoms. Preferably Y represents either hydroxy, or lower alkoxy, or alkoxy-alkoxy, i.e., the respective trichlorophenoxy alkanoic acid or ester thereof, which latter may be hydrolyzed to the free acid, which free acid acid may be readily converted to the salt-form by reaction with an organic or inorganic base.

Since the process of this invention avoids formation of by-product chlorinated dibenzo-p-dioxins, the compounds prepared by the process of this invention would be free of chlorinated dibenzo-p-dioxins, and especially 2,3,7,8-tetrachloro dibenzo-p-dioxin. By free of chlorinated dibenzo-p-dioxin is meant that said dioxins are incapable of detection by known analytic techniques.

The 2,4,5-trichlorophenoxy alkanoic acid esters of this invention are prepared by the liquid phase alkaline condensation of 3-chlorophenol or 3,4-dichlorophenol with an alpha haloalkanoic acid ester preferably in an organic solvent to produce 3-chloro- or 3,4-dichlorophenoxy alkanoic acid ester which is then chlorinated in the liquid phase, to 2,4,5-trichlorophenoxy alkanoic acid ester. The 2,4,5-trichlorophenoxy alkanoic acid ester may be hydrolyzed to the 2,4,5-trichlorophenoxy alkanoic acid which, if desired, may be converted to the salt form by reaction with an organic or inorganic base.

In like fashion, the 2,4,5-trichlorophenoxy acid amides of this invention are prepared by liquid phase alkaline condensation of 3-chlorophenol or 3-4-dichlorophenol with an alpha haloalkanoic acid amide preferably in an organic solvent to produce 3-chloro- or 3,4-dichlorophenoxy alkanoic acid amide which is chlorinated in the liquid phase to 2,4,5-trichlorophenoxy alkanoic acid amide. The 2,4,5-trichlorophenoxy acid amide may be hydrolyzed to 2,4-5 trichlorophenoxy alkanoic acid which in turn may be converted to the salt form by reaction with an organic or inorganic base.

Alternatively 2,4,5-trichlorophenoxy alkanoic acid may be produced directly by liquid phase alkaline condensation of 3-chlorophenol or 3,4-dichlorophenol with an alpha haloalkanoic acid in preferably an aqueous reaction medium to produce 3-chloro- or 3,4-dichlorophenoxy alkanoic acid which is chlorinated in the liquid phase to 2,4,5-trichlorophenoxy alkanoic acid. The acid may be converted to the salt form by reaction with an organic or inorganic base or the salt may be produced directly by reacting 3-chlorophenol or 3,4-dichlorophenol with for example an alkali metal, e.g., sodium, salt of the alpha halo alkali metal acid to produce 3-chloro- or 3,4-dichlorophenoxy alkanoic acid sodium salt which may be chlorinated to 2,4,5-trichlorophenoxy alkanoic acid alkali metal salt.

Regardless whether it is desired to prepare the acid, salt, ester or amide, about equimolar quantities of 3-chlorophenol or 3,4-dichlorophenol and the alpha halo compound are preferably used, although to ensure complete reaction of the phenol group up to about a ten percent molar excess of the alpha halo compound is typically used. Also a molar excess of base, typically up to about 10 percent may also be used in order to ensure complete reaction. Both inorganic as well as organic bases may be used. Exemplary of suitable inorganic bases are the alkali and alkaline earth metal hydroxides, such as sodium hydroxide, potassium hydroxide and calcium hydroxide. Exemplary of organic bases are aliphatic amines such as methylamine, dimethylamine, trimethylamine, ethylamine, diethylamine, tetraethylamine, pyridine, or N,N-dimethylaniline. The alkali metal hydroxides are preferably used.

The reaction between the 3-chlorophenol or 3,4-dichlorophenol and the alpha haloalkanoic acid ester or amide is preferably conducted in an anhydrous or aqueous organic solvent. Preferred solvents are alkyl alcohols such as ethanol, n-propanol, isoproponol, isobutanol, n-butanol, and the like. When preparing 3-chloro- or 3,4 dichlorophenoxy alkanoic acid ester, the alcohol used as a solvent preferably corresponds to the desired ester. Exemplary of other solvents that may be used as the medium for the reaction are acetone, tetrahydrofuran, dimethylformamide and dimethylsulfoxide.

The reaction temperature may vary over a wide range, so long as the temperature is not above the boiling point of the solvent or so low as to result in a prolonged reaction time. Typically the temperature can range from about 10° C. to about 90° C., preferably from about 20° C. to about 60° C.

The reaction between the 3-chlorophenol or 3,4-dichlorophenol and the alpha haloalkanoic acid is preferably conducted in aqueous reaction medium, typically at a temperature of from about 80° C. to about 120° C.

Chlorination of the 3-chloro- or 3,4-dichlorophenoxy alkanoic acid, ester or amide is typically conducted in known fashion in a liquid solvent, e.g., carbon tetrachloride either in the absence of a catalyst or in the presence of a suitable catalyst, such as iodine, metallic iron or tin or ferric chloride.

Hydrolysis of the 2,4,5-trichlorophenoxy alkanoic acid ester or amide to the free acid may be conducted in known fashion by for example treating the amide or ester with an aqueous solution of alkali metal hydroxide or an aqueous solution of a mineral acid.

We claim:

1. In a process for preparing 2,4,5-trichlorophenoxy alkanoic acid, selected from 2,4,5-trichlorophenoxy acetic acid and 2-(2,4,5-trichlorophenoxy) propionic acid including hydrolyzable aliphatic esters and amides of said acids, by reacting in a liquid alkaline reaction medium containing an inorganic or organic base, a chlorinated phenol with at least an equimolar amount of alpha halo compound represented by the formula:

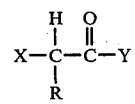

wherein X represents bromine, chlorine or iodine; R represents hydrogen or methyl; and Y represents hydroxy or a hydrolyzable substituent selected from an aliphatic radical containing up to 20 carbon atoms, amide or mono- or disubstituted amide the substituent of which contains up to 20 carbon atoms, and chlorinating the reaction product in the liquid phase, the improvement wherein the alpha halo compound is reacted with a chlorophenol selected from 3-chlorophenol and 3,4-dichlorophenol so as to obtain a pure product that is free of analytically detectable amounts of chlorinated dibenzo-p-dioxins.

2. The improvement of claim 1 wherein the Y substituent of the alpha halo compound is hydroxy and the reaction with the chlorophenol is conducted in aqueous reaction medium at a temperature of from about 80° C. to about 120° C.

3. The improvement of claim 1 wherein the Y substituent of the alpha halo compound is selected from alkoxy and alkoxy-alkoxy containing up to 8 carbon atoms and the reaction with the chlorophenol is conducted in an anhydrous or aqueous organic solvent reaction medium at a temperature of from about 10° C. to about 90° C.

4. The improvement of claim 3 wherein Y is selected from ethoxy, butoxy-ethoxy and iso-octoxy.

5. The improvement of claim 1 wherein the Y substituent of the alpha halo compound is a mono- or disubstituted amide, the substituent selected from alkyl and alkoxy containing up to 8 carbon atoms and the reaction with the chlorophenol is conducted in an anhydrous or aqueous organic solvent reaction medium at a temperature of from about 10° C. to about 90° C.

* * * * *